(12) United States Patent
Cazeneuve

(10) Patent No.: US 11,338,110 B2
(45) Date of Patent: May 24, 2022

(54) FLEXIBLE ELONGATED STRUCTURE HAVING A STEERABLE END

(71) Applicant: BASECAMP VASCULAR, Paris (FR)

(72) Inventor: Jean-Baptiste Cazeneuve, Ivry-sur-seine (FR)

(73) Assignee: BASECAMP VASCULAR, Paris (FR)

( * ) Notice: Subject to any disclaimer, the term of this patent is extended or adjusted under 35 U.S.C. 154(b) by 231 days.

(21) Appl. No.: 16/493,947

(22) PCT Filed: Mar. 16, 2018

(86) PCT No.: PCT/EP2018/056741
§ 371 (c)(1),
(2) Date: Sep. 13, 2019

(87) PCT Pub. No.: WO2018/167300
PCT Pub. Date: Sep. 20, 2018

(65) Prior Publication Data
US 2021/0113814 A1    Apr. 22, 2021

(30) Foreign Application Priority Data
Mar. 16, 2017 (EP) .................................... 17161234

(51) Int. Cl.
*A61M 25/01* (2006.01)
*A61B 1/005* (2006.01)
*A61B 1/01* (2006.01)

(52) U.S. Cl.
CPC ....... *A61M 25/0147* (2013.01); *A61B 1/0057* (2013.01); *A61B 1/01* (2013.01);
(Continued)

(58) Field of Classification Search
CPC .......... A61M 25/0147; A61M 25/0158; A61M 2025/015; A61M 25/0133;
(Continued)

(56) References Cited

U.S. PATENT DOCUMENTS 6,126,633 A  10/2000 Kaji et al.
2013/0211385 A1* 8/2013 Lazarus .......... A61M 2025/015
                                                    604/540
(Continued)

FOREIGN PATENT DOCUMENTS

EP       0815895 A1    1/1998
JP    2010-075530 A    4/2010
(Continued)

OTHER PUBLICATIONS

International Search Report dated Jun. 25, 2018 in corresponding International application No. PCT/EP2018/056741; 11 pages.

*Primary Examiner* — Kami A Bosworth
*Assistant Examiner* — Emily J Becker
(74) *Attorney, Agent, or Firm* — Maier & Maier, PLLC

(57) ABSTRACT

An elongated steerable system for guiding a catheter or an endoscope, comprising: an elongated flexible member including, along at least a part of its longitudinal axis, at least one projection which, in transversal section, projects from the elongated flexible member; the at least one projection having a distal end and a proximal end, and defining, in transversal section, two lateral sides projecting from the elongated flexible member; and a wire; wherein the at least one projection includes at least one transverse retaining and passing element near the distal end of the projection, the retaining and passing element extending transversely to the lateral sides of the projection; and the wire passes through the retaining and passing element alternatively from one lateral side of the projection to the other lateral side of the projection, where adherence between the wire and the retaining and passing element retains the wire.

15 Claims, 3 Drawing Sheets

(52) U.S. Cl.
CPC .............. *A61M 2025/015* (2013.01); *A61M 2205/0216* (2013.01); *A61M 2205/0266* (2013.01)

(58) Field of Classification Search
CPC ...... A61M 25/0138; A61M 2025/0161; A61B 1/0057; A61B 1/0058; A61B 2017/00309; A61B 2017/00323; A61B 1/0055; A61B 1/0056
See application file for complete search history.

(56) References Cited

U.S. PATENT DOCUMENTS

2016/0114132 A1    4/2016  Chmielewski et al.
2016/0278851 A1    9/2016  Mannion et al.

FOREIGN PATENT DOCUMENTS

WO    WO 2012135339 A1 *  10/2012  ........ A61M 25/0105
WO    WO 2016114981 A1 *  7/2016  ...... A61M 2025/015

\* cited by examiner

FLEXIBLE ELONGATED STRUCTURE HAVING A STEERABLE END

FIELD

The present invention relates to a flexible elongated structure having a steerable end. The invention is advantageously applicable in the field of medicine and more particularly for making a catheter or an endoscope. Nevertheless, although it is particularly designed for medical application, the invention may equally well be used in a variety of other technical fields that make use of elongated structures having steerable ends, such as non-destructive inspection of pipes.

BACKGROUND

In known manner, surgeons prefer to use techniques that are not very invasive, making use of narrow access paths in order to treat vascular diseases. Such techniques make it possible to limit recourse to open surgery and they are therefore less burdensome for the patient. For this purpose, use is often made of a catheter or an endoscope that possesses at its distal end a steerable elongated body for the purpose of facilitating insertion and advance of the elongated body inside the human body.

The structure of the elongated body includes at least one actuator member. Said actuator enabling the elongated body end to be curved so as to enable it to negotiate bends and move into non-rectilinear portions of the human body, or in order to view and to treat portions of the body that are not located along the main axis of the elongated body. In general, said actuators are wires, which are fastened to the distal end of the elongated body. Pulling said wire provides a bending of the elongated body.

Various types of actuator member have been proposed, some of which use shape memory alloy wires.

The shape memory alloy wires extend along the elongated body, with their ends being anchored thereto. The shape memory alloy wires are associated with means for heating them, e.g. by Joule effect, thereby causing them to contract in order to cause the elongated body to bend. For this purpose, electrical power supply wires are connected to the shape memory alloy wires.

Nevertheless, such structures are difficult to fabricate. Especially, the wire or the shape memory alloy wire must be fastened at its ends to the longitudinal body.

Various ways of securing shape memory alloy wires to the body have been proposed in US2016/0278851, such as adhesive, welding or chemical bonding, but they are not satisfactory since they do not make it possible to guarantee both that the wire is accurately positioned on the longitudinal body and that it is properly held over time. Besides, these solutions are not satisfactory for a shape memory alloy wire, in particular given the large variations of temperature in the shape memory alloy wire, and the high traction forces to which the shape memory alloy wire is subjected.

It should also be observed that the extra thickness due to the shape memory alloy wires and to the means for connecting said shape memory alloy wires to the body must be minimized so that the assembly presents the compactness needed to enable the structure to pass along ducts of small diameters.

Furthermore, patent application EP0815895 discloses a tubular body comprising a wire which is extended through a lumen for pulling a deformable portion and the distal end of the wire is buried in the wall of the tubular body. But said system comprises a high number of manufacturing steps, which increase the time and difficulty to perform such tubular body. Furthermore, when the wire is a shape memory alloy wire, the distal end of the wire should be connected to a heating means, which is not possible when the distal end of the wire is buried in the wall.

Finally the present invention aims to provide a structure able to pass along ducts of small diameters, easy to manufacture, with an optimal anchorage of the wire to the structure to avoid sliding of the wire ends and to maintain it along the flexible structure body without using additional components such as ligatures or tubes.

SUMMARY

The invention relates to an elongated steerable system for guiding a catheter or an endoscope, comprising:
  an elongated flexible member comprising, along at least a part of its longitudinal axis, at least one projection which, in transversal section, projects from the elongated flexible member; said at least one projection having a distal end and a proximal end, and defining, in transversal section, two lateral sides projecting from the elongated flexible member; and
  a wire;
wherein:
  said at least one projection comprises at least one transverse retaining and passing means near the distal end of said projection, said retaining and passing means extending transversely to the lateral sides of the projection;
  and the wire passes through said retaining and passing means alternatively from one lateral side of the projection to the other lateral side of the projection, wherein adherence between the wire and the retaining and passing means retains the wire ensuring the anchorage of the wire to said retaining and passing means.

According to one embodiment, said at least one projection comprises at least two transverse retaining and passing means.

According to one embodiment, the at least one retaining and passing means is through hole or slit.

According to one embodiment, said at least one retaining and passing means is inclined relative to the longitudinal axis of the elongated flexible member with an angle ranging from 15° to 130°.

According to one embodiment, the longitudinal end of the wire is inclined relative to the longitudinal axis of the elongated flexible member with an angle ranging from 70° to 175°.

According to one embodiment, said wire comprises a distal end and said wire comprises an obstruction or a knot between the distal end of the wire and the at least one retaining and passing means.

According to one embodiment, said obstruction is a crimped element or a tube.

According to one embodiment, the wire is a shape memory alloy wire.

According to one embodiment, the shape memory alloy wire is associated with means for heating the shape memory alloy wire in a controlled manner.

According to one embodiment, the elongated flexible member comprises a superelastic base.

According to one embodiment, the shape memory alloy wire is made of nitinol.

According to one embodiment, the diameter or the width of the retaining and passing means is sensibly equal to or smaller than the wire diameter.

According to one embodiment, the at least one projection is made of polyether ether ketone (PEEK), polyether block amide (PEBAX), polyamide (PA), high-density polyethylene (PEHD) or thermoplastic elastomer (TPE).

According to one embodiment, the length of the projection is smaller than 10% of the length of the elongated flexible member.

According to one embodiment, said projection is made of metal material and the superelastic base is surrounded by an isolating sheath.

According to one embodiment, the number of projections is ranging from 2 to 10, and said projections are regularly arranged around the elongated flexible member.

According to one embodiment, a wire is anchored near the distal end of each projection.

According to a second aspect, the invention relates to an elongated steerable system for guiding a catheter or an endoscope, comprising:
- an elongated flexible member comprising, along at least a part of its longitudinal axis, at least one projection which, in transversal section, projects from the elongated flexible member; said at least one projection having a distal end and a proximal end, and defining, in transversal section, two lateral sides projecting from the elongated flexible member; and
- a wire;

wherein:
- said at least one projection comprises at least one transverse passing means near the distal end of said projection, said retaining and passing means extending transversely to the lateral sides of the projection;
- and the wire passes through said passing means alternatively from one lateral side of the projection to the other lateral side of the projection, wherein said wire comprises a distal end and said wire comprises an obstruction or a knot between the distal end of the wire and the at least one transverse passing means.

Definitions

In the present invention, the following terms have the following meanings:

"Flexible" has to be understood as being capable to be curved at least at 30° by the wire contraction, optionally 40°, 50°, 60°, 70°, 80°, 90° or 100°, and elastically return to its original shape.

"Longitudinal axis" refers to the axis along the longest direction of an element.

"Transversal section" refers to the section which is orthogonal to the longitudinal axis.

"Concave" refers to a surface curved like the inner surface of a sphere or a surface having at least one internal angle smaller than 180 degrees.

"Distal end" refers to the longitudinal extremity of an elongated element which is situated away from the point of attachment.

"Proximal end" refers to the longitudinal extremity of an elongated element which is situated in the vicinity of the point of attachment.

BRIEF DESCRIPTION OF THE DRAWINGS

The present invention can be better understood on reading a detailed description of an embodiment given with reference to the accompanying drawings that are provided by way of non-limiting example, and in which.

DETAILED DESCRIPTION

The first aspect of the invention relates to an elongated steerable system 1 for guiding a catheter or an endoscope. According to the present invention, the elongated steerable system 1 comprises an elongated flexible member 10 and a wire 20.

Figure 1:
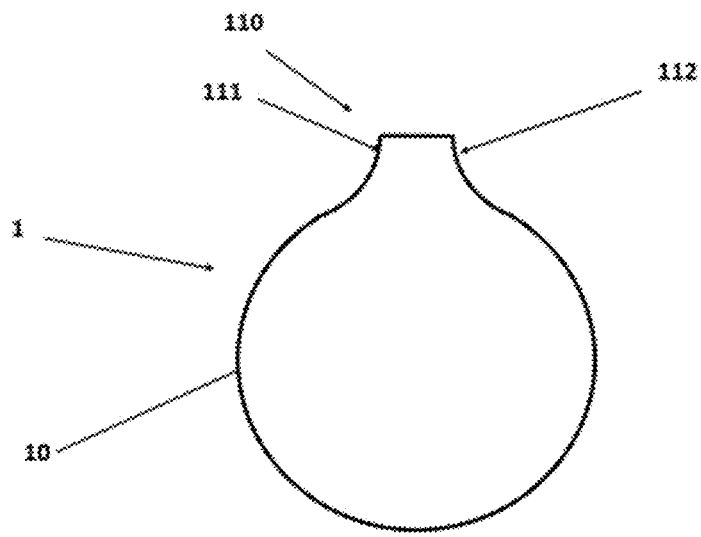
FIG. 1 is a drawing of a transversal section of the elongated flexible member.

The elongated flexible member 10 is a longitudinal body comprising a distal end and a proximal end. As illustrated in FIG. 1, the transversal section of the elongated flexible member 10 is not circular or rectangular. The elongated flexible member 10 comprises at least one projection 110 along at least a part of its longitudinal axis. In transversal section to the longitudinal axis, said projection 110 projects outwardly from the elongated flexible member 10. Said projection 110 could be a relief or an embossed design on the elongated flexible member 10 transversal section design. According to one embodiment, the transversal section of the elongated flexible member 10 is regular and unchanging along at least a part of its longitudinal axis. According to another embodiment, the transversal section of the elongated flexible member 10 is regular and unchanging along its entire length.

According to one embodiment, the elongated flexible member 10 has a steerable distal end.

According to one embodiment, the elongated flexible member 10 is superelastic. According to one embodiment, the elongated flexible member 10 comprises a superelastic base 12 (also called pseudoelastic base) which is surrounded by a plastic material.

The term "superelastic base" refers here to a core of the elongated flexible member 10 made of superelastic material.

Said plastic material is molded or extruded to design the shape of the elongated flexible member 10 section. According to one embodiment, the superelastic base 12 is surrounded by a material made of polyether ether ketone (PEEK), polyether block amide (PEBAX®), polyamide (PA), high-density polyethylene (PEHD) or thermoplastic elastomer (TPE). According to one embodiment, the projection 110 is designed in the plastic material.

Figure 6:
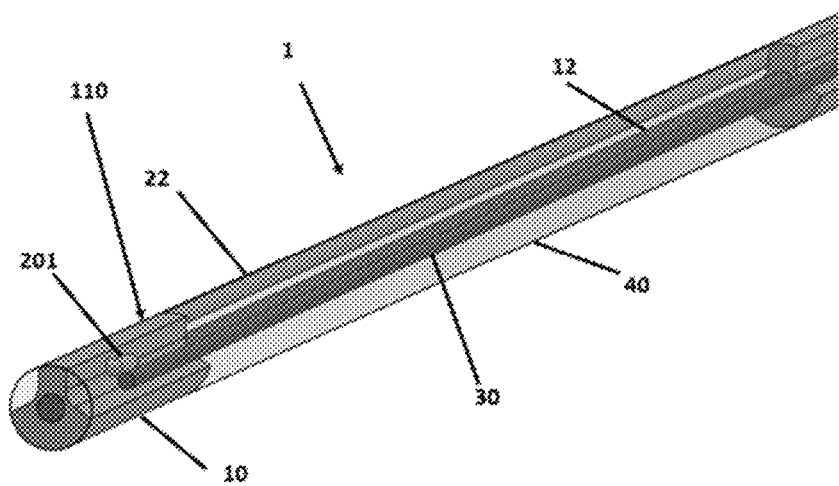
FIG. 6 is a perspective view of the elongated steerable system according to one embodiment wherein the projection does not cover the entire length of the elongated flexible member.

According to another embodiment, illustrated in FIG. 6, the elongated flexible member 10 comprises a superelastic base 12 which is surrounded by at least one projection 110 on the vicinity of the distal end of the elongated flexible member 10. According to said embodiment, the projection 110 is fixed to the superelastic base 12 at the distal end of the elongated flexible member 10. According to said embodiment, said projection 110 is fixed to the superelastic base 12.

According to one embodiment, said projection is fixed to the superelastic base 12 by bonding or gluing. According to one embodiment, the projection 110 can be made of any material, including metal. According to one embodiment, the superelastic base 12 is surrounded by an isolating sheath to prevent any electric conduction between the superelastic base 12 and the projection 110 when said projection 110 is made of a conductive material.

According to one embodiment, the elongated flexible system 1 comprises at least one projection at its distal end and optionally on its entire length. Said embodiment provides a lighter structure.

According to one embodiment, the superelastic base 12 is a nickel titanium alloy or a nitinol. Such superelasticity will improve the guidance of the elongated steerable system 1. Indeed, during the contraction of the wire 20, the distal end of the elongated flexible member 10 will be curved. To reorient the distal end as its original shape, the operator has to reduce the contraction on the wire 20 and the superelasticity increases the speed of the return.

The projection 110 defines two lateral sides 111 and 112 along the longitudinal axis of the elongated flexible member 10, which, in transversal section, project outwardly from the elongated flexible member 10. Said lateral sides are configured to receive the wire 20, which may be a shape memory alloy member. Said projection 110 comprises a distal end and a proximal end wherein the distal end of said projection 110 is on the same side as the distal end of the elongated flexible member 10.

According to one embodiment, the projection 110 runs along the whole or a part of the length of the elongated flexible member 10. By "a part of", we means here at least 80%, at least 70%, at least 60%, at least 50%, at least 40%, at least 30%, at least 20%, or at least 10% of the length of the elongated flexible member 10. According to one embodiment, the projection 110 is made of the surrounding material around the superelastic base 12. According to one embodiment, said projection 110 is made of polyether ether ketone (PEEK), polyether block amide (PEBAX®), polyamide (PA), high-density polyethylene (PEHD) or thermoplastic elastomer (TPE).

According to another embodiment illustrated in FIG. 6, the length of the projection 110 is smaller than 10% of the length of the elongated flexible member 10 or is smaller than 5%, 4%, 3% or 2% of the length of the elongated flexile member. According to one embodiment, the projection 110 has a length along the longitudinal axis of the elongated flexible member ranging from 5 and 100 mm, from 7 and 70 mm, from 10 and 50 mm, or from 15 and 40 mm. In said embodiment, the at least one projection 110 is made of any material, preferably in metal.

According to one embodiment illustrated in FIG. 1, said two lateral sides 111 and 112 are curved in order to form two concave surfaces.

Figure 3:
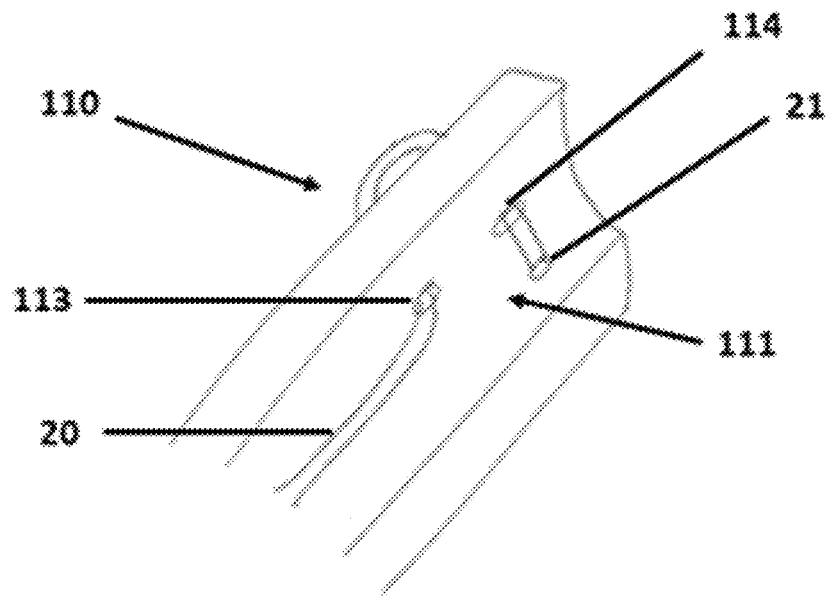
FIG. 3 is a perspective view of the distal end of the projection according to one embodiment wherein the retaining and passing means are through holes.
Figure 4:
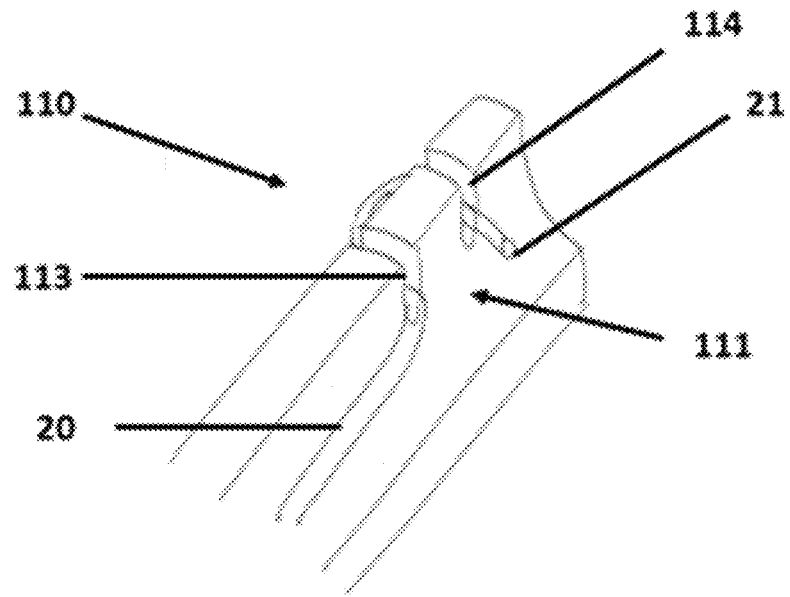
FIG. 4 is a perspective view of the distal end of the projection according to one embodiment wherein the retaining and passing means are slits.

As illustrated in FIG. 3 and FIG. 4, the projection 110 comprises at least one transverse retaining and passing means 114 extending transversely to the lateral sides 111 and 112 of the projection. According to one preferred embodiment, the projection 110 comprises at least two transverse retaining and passing means 113, 114. According to one embodiment, the number of retaining and passing means 113, 114 can be higher than 2, as each 180° curvature between two retaining and passing means 113, 114 improves the static friction during the wire 20 contraction. According to one embodiment, the projection 110 comprises at least 3, 4, 5, 6, 7, 8, 9, or 10 retaining and passing means.

Said at least one transverse retaining and passing means 114 will ensure an anchorage with the wire 20.

Said at least one retaining and passing means 114, or at least two retaining and passing means are located near the distal end of said projection 110. The term "near the distal end" refers to a region at the distal end of the projection 110, said region is not necessarily in contact with said distal end but is close enough to ensure the curvature of the distal end of the elongated flexible member 10 when a strain is applied on the wire 20.

The wire 20 passes through said retaining and passing means 114 alternatively from one lateral side of the projection 111 to the other lateral side of the projection 112. The adherence between the wire 20 and the at least one retaining and passing means 114 retains the wire 20 ensuring the anchorage of the wire 20 to said retaining and passing means 113, 114 near the distal end of said projection 110.

The wire 20 and the at least one retaining and passing means 114 are configured to create a static friction that needs to be overcome to enable relative motion or to enable the sliding, between said wire 20 and said at least one retaining and passing means 114. The two contact surfaces (the wire one and the retaining and passing means one) adhere one to the other avoiding sliding during the wire 20 contraction.

According to one embodiment, said at least one retaining and passing means 114 is small enough to create static friction. According to one embodiment, the diameter of said through holes or the width of said slits are sensibly equal to or smaller than the diameter of the wire 20. By "sensibly equal to", we refers to a diameter or a width equal to the diameter of the wire 20 or within a range of the diameter at more or less 15%, preferably 10%, and very preferably 5%.

According to one embodiment, said at least one retaining and passing means 114 is a through hole as illustrated in FIG. 3 or slit as illustrated in FIG. 4.

According to one embodiment, the diameter of said through holes or the width of said slits ranges from 50 µm to 1000 µm, from 100 µm to 500 µm or from 150 µm to 250 µm.

According to one embodiment, the at least one retaining and passing means 114 is inclined relative to the longitudinal axis of the elongated flexible member 10 with an angle ranging from 15° to 130°. The inclination of said at least one retaining and passing means 114 contributes to the adherence and to improve the static friction between the surface of said at least one retaining and passing means 114 and the surface of said wire 20.

Preferably, the at least one retaining and passing means 114 is inclined relative to the longitudinal axis of the elongated flexible member 10 with an angle ranging from 80° to 100°. According to one embodiment, the wire 20, when activated, will try to take a rectilinear shape. In this way, the wire 20 will apply a force at the contact on the at least one transverse retaining and passing means 114 which ensures the anchorage.

According to one embodiment wherein the wire 20 is a shape memory alloy wire, and the activation is provided by heating said shape memory alloy wire. When said shape memory alloy wire is heated, it will try to return to its original straight shape. In this way, the shape memory alloy wire will apply a force at the contact on the at least one transverse retaining and passing means 114 which ensures the anchorage.

According to one embodiment, the projection 110 comprises at least two transverse retaining and passing means 113, 114. With at least two transverse retaining and passing means, the wire 20 has to make at least one 180° curve between two retaining and passing means 113, 114 which increases the static friction, in particular when the wire 20 is pulled and tries to take a rectilinear straight shape or when the shape memory alloy wire is heated and tries to return to its original straight shape.

Figure 2:
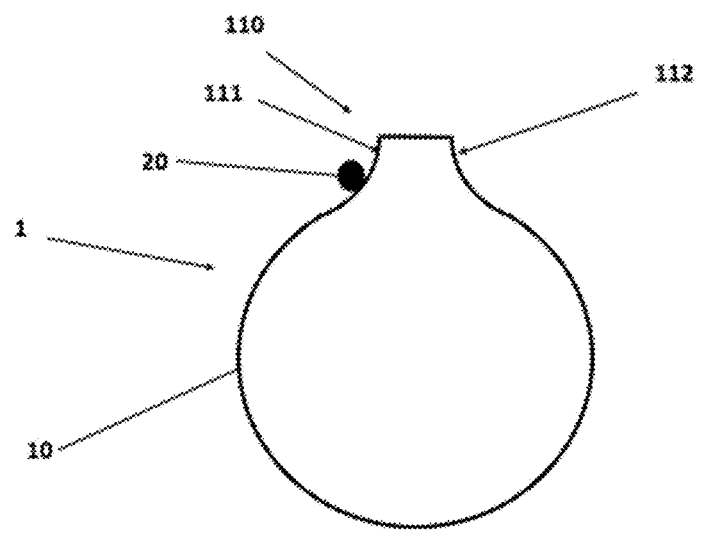
FIG. 2 is a drawing of a transversal section of the elongated flexible member and the wire.

The wire 20 extends along the length of the elongated flexible member 10. As illustrated in FIG. 2, the wire 20 extends along lateral sides of the projection 111 and/or 112.

The wire 20 comprises a distal end 21, and said distal end 21 is anchored to the distal end of the projection 110. The wire 20 passes through the at least one retaining and passing means 114 and passing alternatively from one lateral side of the projection 111 to the other side of the projection 112. Said at least one retaining and passing means 114 retains the wire 20 ensuring the anchorage.

According to one embodiment, the distal end 21 of the wire 20 is inclined relative to the longitudinal axis of the elongated flexible member 10 with an angle ranging from 70° to 175°, preferably ranging from 80° to 120°. This inclination contributes to the static friction between the wire 20 and the at least one retaining and passing means 114.

Figure 5:
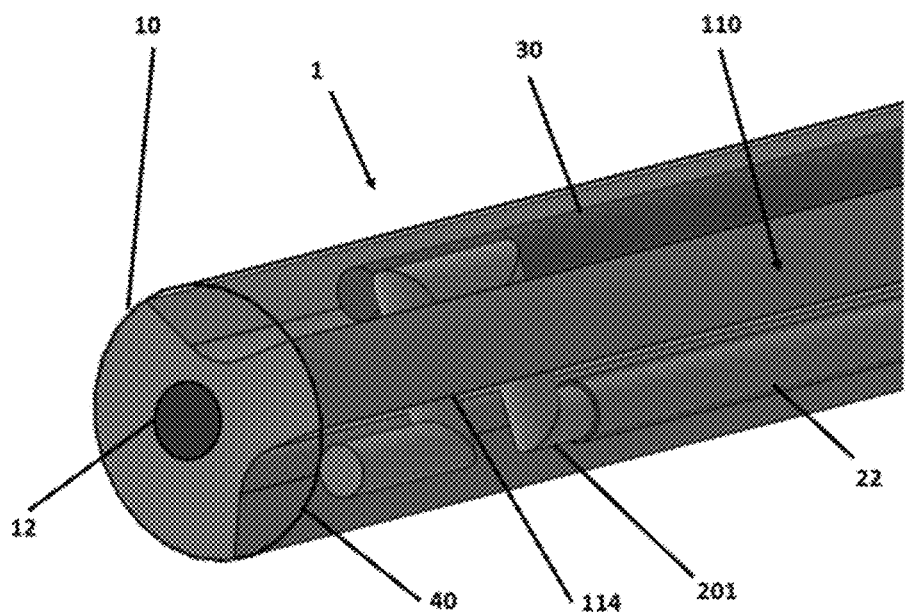
FIG. 5 is a perspective view of the distal end of the elongated steerable system according to one embodiment.

According to one embodiment wherein the wire is a shape memory alloy wire, the elongated steerable system 1 further comprises a shape memory alloy wire's sheath 22, as illustrated in FIG. 5, to receive the shape memory alloy wire 201 along at least a part of the lateral sides of the projection 111 and/or 112. This sheath 22 is used to create a thermal isolation between the projection 110 and the shape memory alloy wire 201.

According to one embodiment, the shape memory alloy wire 201 is associated with means fort heating the shape memory alloy wire 201 in a controlled manner (e.g. by Joule effect). Such controlled heating providing the contraction of the shape memory alloy wire 201 and the flexion of the distal end of the elongated steerable system 1.

According to one embodiment, the shape memory alloy wire 201 is made of, or comprises, a nickel titanium alloy such as nitinol.

According to one embodiment, the wire 20 has a diameter ranging from 10 μm to 1000 μm, ranging from 50 μm to 500 μm or ranging from 50 μm to 400 μm.

In one embodiment wherein the wire 20 is a shape memory alloy wire, the elongated steerable system 1 comprises heating means. In one embodiment, electrical power supply wires are connected to the shape memory alloy wire 201. In one embodiment illustrated in FIG. 5, the heating means is a conductive electric wire 30. Preferably, the shape memory alloy wire 201 is connected electrically to a conductive electric wire 30 at the portion of the shape memory alloy wire 201 located between two retaining and passing means 113 and 114 or near to the at least one retaining and passing means 114.

According to one embodiment, the shape memory alloy wire 201 is connected electrically to a second conductive electric wire 30 at the portion of the proximal end of the shape memory alloy wire 201. By applying a voltage between the two conductive electric wires, the shape memory alloy wire 201 is heated with a controlled manner, providing its contraction and the flexion of the elongated steerable system 1.

According to one embodiment, the conductive electric wire 30 extends from the proximal end of the at least one projection 110 to the distal end of the projection 110 along one lateral side 111 or 112, optionally the lateral side opposite to the lateral side wherein the shaped memory alloy wire extends.

Preferably, the conductive electric wire 30 is a copper wire. According to one embodiment, the conductive electric wire 30 is associated to the shape memory alloy wire 201 by a weld or a soldered joint. According to one embodiment, the shape memory alloy wire 201 is weld at a copper wire at its both distal and proximal ends.

According to one embodiment, the projection 110 of the elongated flexible member 10 further comprises at least one transverse passing means. This at least one passing means creates a hole or a slit through the projection 110 between the proximal end of said projection 110 and the at least one retaining and passing means 114.

In said embodiment, the wire 20 passes through said transverse passing means alternatively from one side of the projection 111 to the other side of the projection 112.

By "transverse passing means", we mean here means that does not contribute to create a static friction. According to one embodiment, these transverse passing means are through holes or slits. The wire 20 is able to slide relative to said transverse passing means. The passing means and the wire 20 have to not create a static friction. Indeed, the wire 20 has to slide during its contraction to provide the flexion of the elongated flexible member 10. According to one embodiment, the diameter or the width of said transverse passing means is higher than the diameter or the width of the wire 20.

Said passing means prevent the wire 20 from rotating around the elongated flexible member 10 during the use of the elongated steerable system 1. In such a way, the elongated steerable system 1 does not need ligatures to maintain the wire 20 as in the prior art. The additional transverse passing means ensure the radial and tangential holding of the wire 20 during the flexion of the elongated flexible member 10. The lateral sides 111 and 112 of the projection and the at least one transverse passing means prevent separation of the wire 20 and elongated flexible member 10 while the wire 20 is pulled, activated or heated.

According to one embodiment, the wire 20 further comprises an obstruction or a knot between the distal end 21 of the wire and the at least one retaining and passing means in in order to improve the anchorage to the distal end of the projection 110.

In one embodiment, said obstruction is an element which has a higher section or has higher dimensions than the section or the dimensions of the retaining and passing means 114 and said obstruction or said knot cannot pass through the retaining and passing means 114. Indeed, during the handle of the elongated steerable system 1, the operator may pull the wire 20 by applying a strength high enough providing the sliding of the wire 20 relative to the at least one retaining and passing means 114 in spite of the static friction. Said obstruction, or said knot prevents the removal of the wire 20. This obstruction or knot is an additional security for the anchorage.

According to one embodiment, said obstruction is a crimped element or a tube secured to the distal end 21 of the wire 20 after the distal end has been passed through the at least one retaining and passing means 114. According to one embodiment, said obstruction is a geometric protrusion on the distal end 21 of the wire. According to one embodiment, said geometric protrusion is formed by welding or melting the distal end 21 of the wire.

According to one embodiment, the elongated flexible member 10 further comprises an opening between the retaining and passing means 114 and said obstruction or knot, the wire 20 passing through said opening. According to one embodiment, said opening has a width or a diameter smaller than the diameter or the width of the obstruction or the knot. The opening can have a round, a square, a rectangular section or similar section. The obstruction can be glued on or welded to the opening.

According to one embodiment, said obstruction is a flattened portion of the wire. According to one embodiment, said flattened portion has a width higher than the width or the diameter of the rest of the wire 20 and further higher than dimensions of the retaining and passing means or said opening. Said flattened portion can be achieved by pressing.

According to one embodiment, the elongated flexible member further comprises a bar or a pin in the vicinity of the distal end of the elongated flexible member. According to one embodiment, the flattened portion of the wire is wrapped around said pin or said bar. Said flattened portion of the wire can be folded over itself, can be welded or soldered or mechanically fastened to the distal end of the elongated flexible member 10, to said bar or said pin, or to said opening.

In an alternative embodiment, a knot is made at the distal end 21 of the wire 20 after the distal end has been passed through the at least one retaining and passing means 114.

According to one embodiment, the proximal end of the wire 20 is anchored to the proximal end of the projection 110 or anchored to the proximal end of the elongated flexible member 10. According to one embodiment the anchorage of the proximal end of the wire 20 to the proximal end of the projection 110 is similar to the anchorage of the wire 20 to the distal end of the projection 110 according to the present invention.

According to one embodiment illustrated in FIG. 5, the elongated steerable system 1 further comprises a heat-shrink tubing 40. Said heat-shrink tubing 40 is a sheath protecting all the elements of the elongated steerable system 1 and improving the sliding of the elongated steerable system 1 inside the human body.

According to one embodiment, the sheath 22 is used to create a thermal isolation between said heat-shrink tubing 40 and the wire 20.

According to one embodiment, the elongated flexible member 10 comprises at least two projections 110 and at least two wires 20. According to one embodiment, the elongated flexible member 10 comprises at least two projections 110 along at least a part of its longitudinal axis according to the present invention and one wire 20 according to the present invention for each projection 110. In one embodiment, the several projections 110 are regularly arranged around the elongated flexible member 10. According to one embodiment, a wire 20 can be used on two projections. In said embodiment, a first longitudinal end of the wire is fixed to one projection according to the present invention, and the second longitudinal end of said wire is fixed to a second projection according to the present invention.

According to one embodiment, the number of projections 110 is ranging from 2 to 10. According to an embodiment, said projections 110 are regularly arranged around the elongated flexible member 10. According to one embodiment, a wire 20 is anchored near the distal end of each projection 110. According to one embodiment, both longitudinal distal end of the wire 20 are anchored to a distal end of one projection 110.

According to a second aspect of the invention, the projection comprises at least one passing means near to the distal end of the projection and the wire passes through a passing means and the anchorage is provided by a knot or by an obstruction on the distal end of the wire. According to one embodiment, the distal end of the wire comprises an element larger than the passing means. Said element larger than the passing means enables the wire to get out said passing means. In one embodiment, said obstruction is a crimped element or a tube secured to the distal end 21 of the wire 20 after the distal end has been passed through the at least one passing means. In one embodiment, said knot or said obstruction is between said passing means and the distal end of the wire. According to one embodiment, said obstruction or said knot can be according to any of the embodiments described previously in the first aspect of the invention.

The invention claimed is:

1. An elongated steerable system for guiding a catheter or an endoscope, comprising:
   an elongated flexible member comprising, along at least a part of its longitudinal axis, at least one projection which, in a transversal section, projects from the elongated flexible member; said at least one projection having a distal end and a proximal end, and defining, in the transversal section, two lateral sides projecting from the elongated flexible member; and
   a wire; wherein:
   said at least one projection comprises at least one lateral retaining and passing means near the distal end of said at least one projection, said at least one lateral retaining and passing means extending transversely to the lateral sides of the at least one projection;
   and the wire passes through said at least one lateral retaining and passing means alternatively from one lateral side of the at least one projection to the other lateral side of the at least one projection, wherein adherence between the wire and the at least one lateral retaining and passing means retains the wire ensuring the anchorage of the wire to said at least one lateral retaining and passing means.

2. The elongated steerable system according to claim 1, wherein said at least one projection comprises at least two lateral transverse retaining and passing means.

3. The elongated steerable system according to claim 1, wherein the at least one lateral retaining and passing means is a through hole or slit.

4. The elongated steerable system according to claim 1, wherein said at least one lateral retaining and passing means is inclined relative to the longitudinal axis of the elongated flexible member with an angle ranging from 15° to 130°.

5. The elongated steerable system according to claim 1, wherein a longitudinal end of the wire is inclined relative to the longitudinal axis of the elongated flexible member with an angle ranging from 70° to 175°.

6. The elongated steerable system according to claim 1, wherein said wire comprises a distal end and said wire comprises an obstruction or a knot between the distal end of the wire and the at least one lateral retaining and passing means.

7. The elongated steerable system according to claim 1, wherein said wire is a shape memory alloy wire.

8. The elongated steerable system according to claim 7, wherein the shape memory alloy wire is associated with means for heating the shape memory alloy wire in a controlled manner.

9. The elongated steerable system according to claim 1, wherein the elongated flexible member comprises a superelastic base.

10. The elongated steerable system according to claim 9, wherein said at least one projection is made of metal material and the superelastic base is surrounded by an isolating sheath.

11. The elongated steerable system according to claim 1, wherein a diameter or a width of the at least one lateral retaining and passing means is equal to or smaller than a diameter of the wire.

12. The elongated steerable system according to claim 1, wherein a length of the at least one projection is smaller than 10% of a length of the elongated flexible member.

13. The elongated steerable system according to claim 1, wherein the number of projections ranges from 2 to 10, and wherein said projections are regularly arranged around the elongated flexible member.

14. The elongated steerable system according to claim 13, wherein a wire is anchored near the distal end of each of the 2 to 10 projections.

15. An elongated steerable system for guiding a catheter or an endoscope, comprising:

an elongated flexible member comprising, along at least a part of its longitudinal axis, at least one projection which, in a transversal section, projects from the elongated flexible member; said at least one projection having a distal end and a proximal end, and defining, in the transversal section, two lateral sides projecting from the elongated flexible member; and a wire; wherein:

said at least one projection comprises at least one lateral passing means near the distal end of said at least one projection, said at least one lateral passing means extending transversely to the lateral sides of the at least one projection;

and the wire passes through said at least one lateral passing means alternatively from one lateral side of the at least one projection to the other lateral side of the at least one projection, wherein said wire comprises a distal end and said wire comprises an obstruction or a knot between the distal end of the wire and the at least one lateral passing means.

\* \* \* \* \*